United States Patent [19]

Zuckerman

[11] Patent Number: 4,648,260

[45] Date of Patent: Mar. 10, 1987

[54] HELIUM DETECTOR

[75] Inventor: Matthew M. Zuckerman, Sunnyvale, Calif.

[73] Assignee: Mark Telephone Products, Inc., Santa Clara, Calif.

[21] Appl. No.: 736,482

[22] Filed: May 20, 1985

[51] Int. Cl.[4] ............................................ G01N 30/02
[52] U.S. Cl. ..................................... 73/23.1; 73/27 R
[58] Field of Search ............... 73/23.1, 27 R, 40.7; 364/497; 55/67, 197, 386; 436/56, 161; 422/89

[56] References Cited

U.S. PATENT DOCUMENTS

| 2,687,036 | 8/1954 | Minter | 73/27 R |
|---|---|---|---|
| 3,447,360 | 6/1969 | Laseter | 73/23.1 |
| 3,527,926 | 9/1970 | Holy | 73/23.1 |
| 3,714,421 | 1/1973 | Josias et al. | 73/23.1 |
| 3,717,028 | 2/1973 | Annino et al. | 73/23.1 |
| 3,786,675 | 1/1974 | Delatorre et al. | 73/27 R |
| 4,145,506 | 3/1979 | Yamamoto et al. | 55/386 |
| 4,229,968 | 10/1980 | Muldoon | 73/23.1 |

Primary Examiner—Stephen A. Kreitman
Attorney, Agent, or Firm—Townsend and Townsend

[57] ABSTRACT

A method of detecting a component gas of a gaseous mixture, and apparatus implementing the method, is disclosed. The method includes passing the mixture through a fixed-phase separator to produce an effluent in which the components are consigned, in ordered [time-related] fashion, to predetermined portions of the effluent. That portion of the effluent containing the component gas to be detected is monitored to produce a measurement indicative of the quantity of the component gas in the mixture.

5 Claims, 6 Drawing Figures

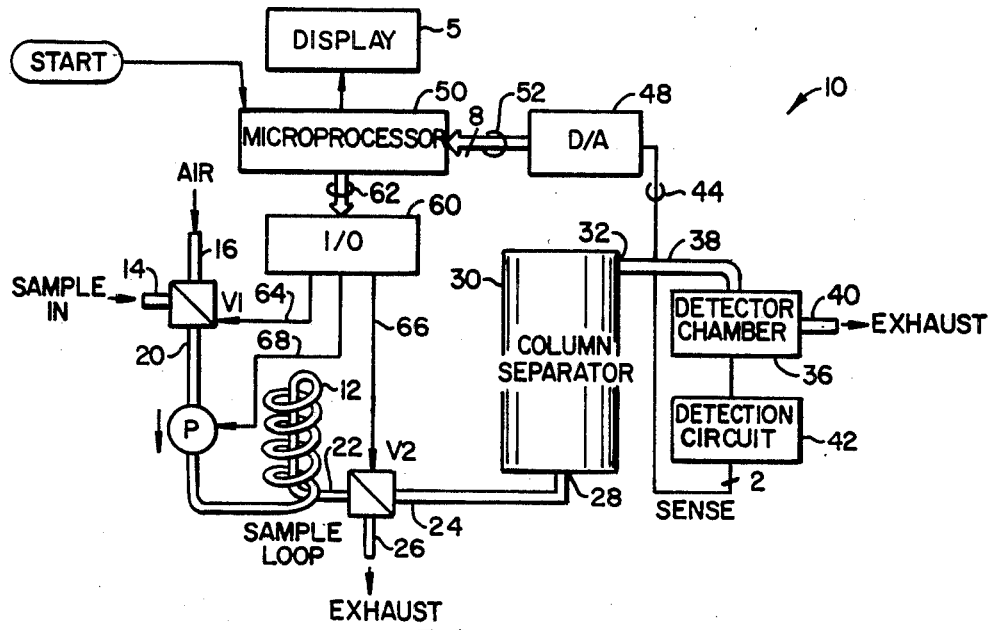
FIG._2.
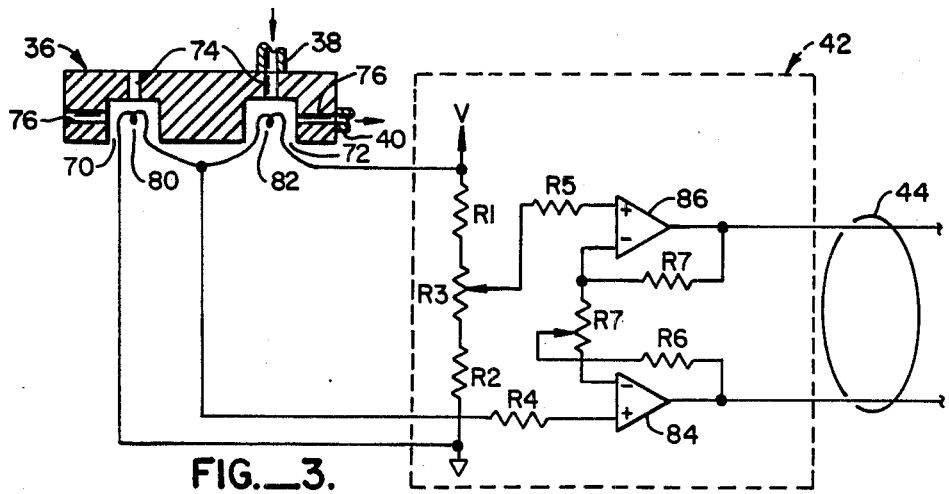
FIG._3.
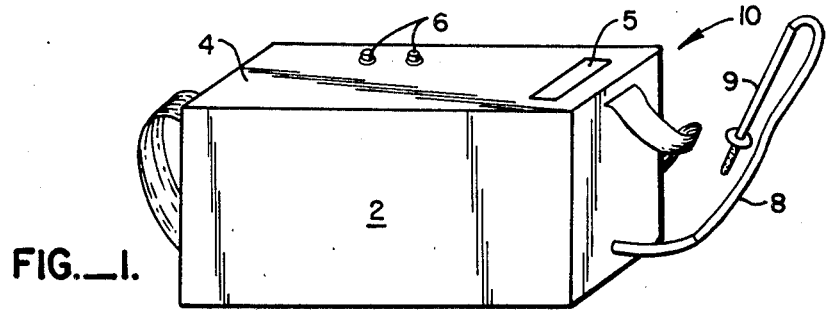
FIG._1.

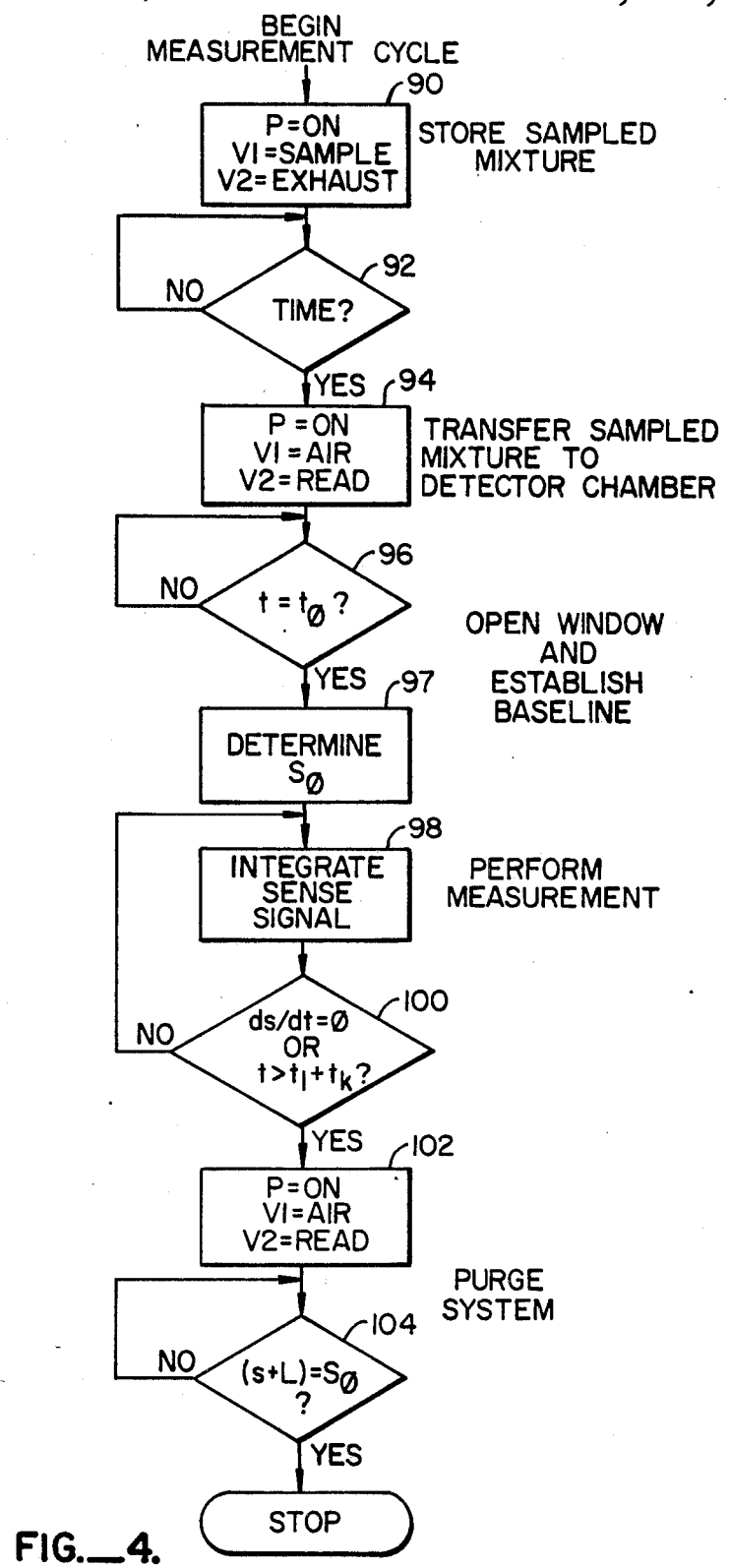
FIG._4.

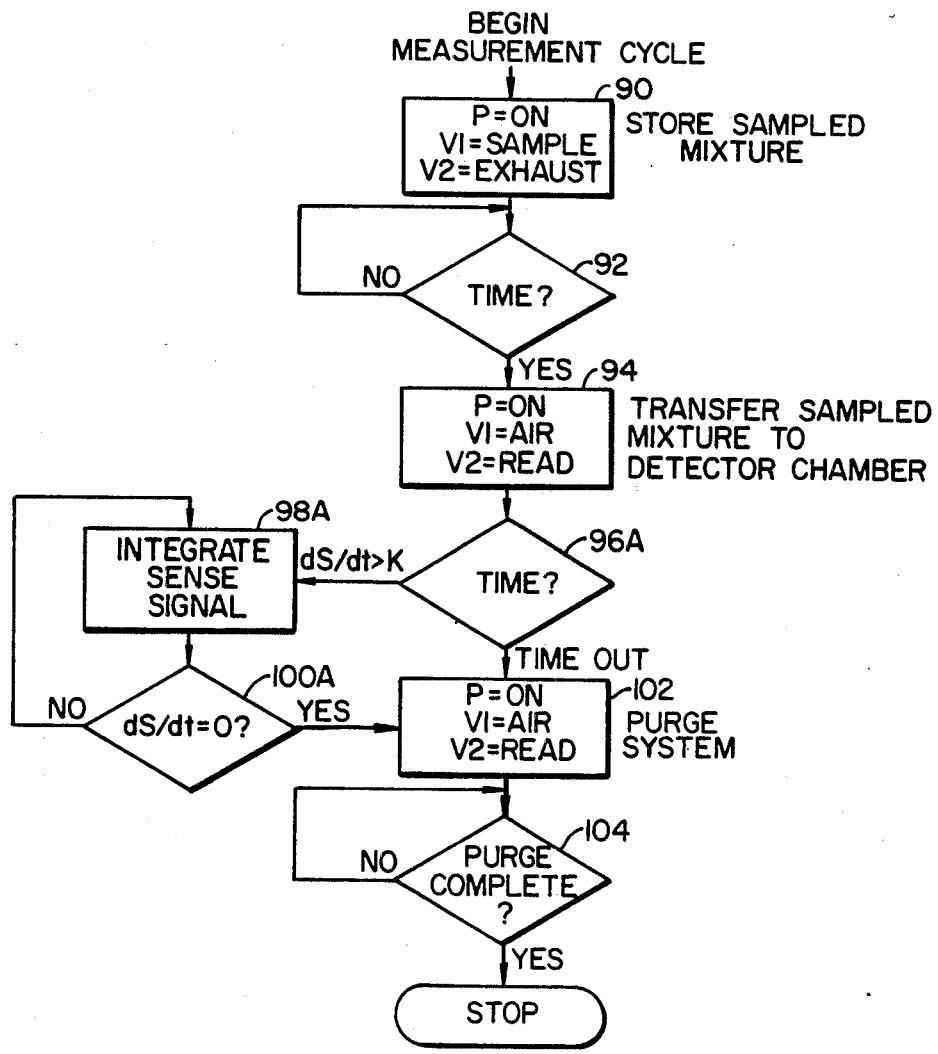
FIG._6.
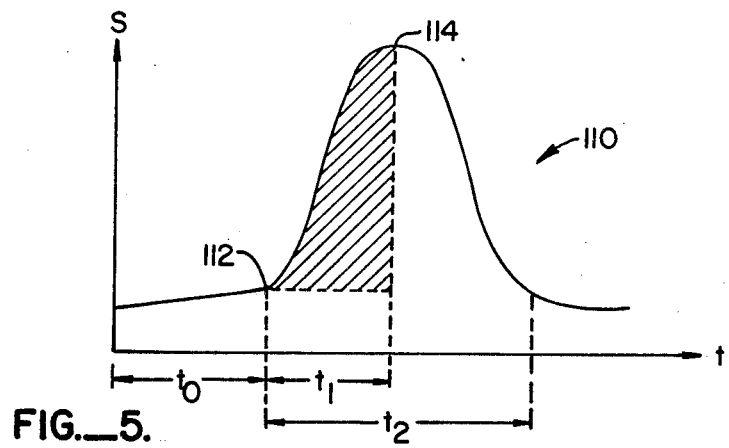
FIG._5.

HELIUM DETECTOR

BACKGROUND OF THE INVENTION

The present invention is directed to detection of a component gas contained in a mixture of gases. More specifically, the invention is a method, and apparatus that implements that method, that detects helium tracer gas for locating leaks in underground telephone cables.

Telephone cables, to prevent water from shorting pairs of the wires that make up the cables, are usually enclosed in a sheath and internally pressurized with dry air compressors placed at predetermined locations along the cable. Unfortunately, there are times when the sheath is penetrated, either by chemical degradation (electrolysis), mechanical stresses, or similar phenomena, causing leaks in the sheath and allowing the introduction of water. This, in turn, causes a degradation of any internal insulation, permitting deterioration and shorting of the internal wiring, and degradation of the signals carried by the cable. Repairing this damage can cost substantial sums because it is sometimes necessary to excavate in several points or trench hundreds of yards of cables due to the impossibility of identifying the exact location of the leak.

Recent techniques have been developed to more accurately pinpoint the location of leaks that develop in the cable sheath in order to minimize the amount of cable that must be unearthed and replaced. One technique that has been found sufficiently successful to enjoy common use today is one that includes the step of obtaining a preliminary rough location of the leak by taking pressure measurements of the cable. The resolution of this technique can locate the leak within anywhere from 300 feet to 6,000 feet. The cable, at periodic locations, is then pressurized with a helium tracer gas, and a helium detector used to pinpoint the leak more accurately by detecting the helium that permeates to the surface of the ground from the leak. One technique of detection is by use of a helium mass spectrometer.

While the use of helium mass spectrometers have been somewhat reliable, mass spectrometers themselves are not without certain problems. Their operation depends upon separation of the helium gas in a vacuum by imparting an electrical charge to the gas sample containing the helium, pushing the sample through a magnetic field, and collecting the hydrogen ions from the result. The electronics, including a supply of high voltage, and the vacuum system make this type of helium detector bulky, complicated and expensive. Since leaks are just as prone to developing in relatively remote areas where access to such heavy equipment can be difficult, the efficacy of this leak-detection technique becomes limited.

Helium tracer gas detection is also performed using negative-going combustible gas detectors. These devices, however, lack the sensitivity necessary for use in tracer gas detection, making this type of detection technique less effective than desired.

SUMMARY OF THE INVENTION

The present invention provides a method of quickly detecting the presence of component gas, such as helium, in a sample gas mixture. The method is capable of being implemented in the apparatus aspect of this invention, which is a compact, lightweight, and relatively inexpensive device, capable of being easily carried by one person, even in rugged terrain, and used to quickly detect the component gas being searched.

According to the method aspect of the invention, a predetermined sample of a gas mixture is passed through a fixed-phase separator configured to "order," i.e., relatively position, the individual component gases of the mixture, especially the component gas being searched for, in the separator's effluent. Preferably, the component gases are ordered on the effluent so that in that ordering the component gas being searched for will exit first from the separator. The rate of change of the thermal conductivity of the effluent is monitored, and, at about the same time, the thermal conductivity is measured (i.e., integrated) over time until the rate of change goes to zero. The measurement obtained provides a relatively accurate indication of the quantity of the searched for component gas contained in the sampled mixture.

Apparatus incorporating the invention is disclosed. In the preferred embodiment the method and apparatus of the invention is directed to detection of a tracer gas so that the invention can advantageously be used to assist in detecting leaks in telephone cable sheaths. The apparatus includes a microprocessor-controlled system, including a fixed-phase separator, for sampling a gas mixture to determine if the sample includes the searched for component gas, i.e., helium. The fixed-phase separator is configured to retard those component gases sufficiently to allow any helium gas to be encountered first (in time) in the effluent from the separator. The effluent is passed through a detector chamber that produces a signal indicative of the thermal conductivity of the effluent. The rate of change of the signal is monitored during the first portion of the effluent and, at a predetermined point in time, the signal is integrated over time until the rate of change becomes approximately zero at which point the integration process stops. The integration process develops a measurement that is indicative of the quantity of helium gas, which is displayed to the user. In an alternate embodiment of the invention the integration process is initiated when the rate of change of the effluent's thermal conductivity exceeds a predetermined level, terminating as before when the rate of change becomes approximately zero.

The detector chamber includes a pair of hot wires arranged in a bridge circuit and each mounted in a corresponding cavity of the detector chamber. One hot wire functions as a reference, and is open to the atmosphere; the other has the effluent passed thereacross. A voltage indicative of the imbalance of the bridge is converted to digital information and applied to the microprocessor which, in addition to supervising system operation, produces the measurement indicative of the quantity of gas contained in the sample.

A number of advantages are achieved by the present invention. First, since the method disclosed does not require a vacuum or high voltages (of the type used by mass spectometers) the method can be implemented in a compact, lightweight unit that can be easily carried by one person. Accordingly, the invention is particularly advantageous for use in the field for telephone cable leak detection.

In addition, the invention provides a relatively accurate indication of the quantity of helium, thereby allowing a user to more accurately pinpoint an underground cable leak in a procedure using helium tracer gas.

These and other advantages of the present invention will become apparent to those skilled in the art upon a reading of the following detailed description, which should be taken in conjunction with the accompanying drawings.

BRIEF DESCRIPTION OF THE DRAWINGS

FIG. 1 is a perspective view of a helium detector constructed in accordance with the teachings disclosed herein, illustrating the capability of implementing both the method and apparatus aspects of the invention in a compact unit;

FIG. 2 is a block diagram representation of the system incorporating the present invention;

FIG. 3 is a schematic representation of the detector chamber and detector circuit used to generate a voltage indicative of the thermal conductivity of the effluent produced by the system of FIG. 1;

FIG. 4 is a flow chart illustrating the steps taken by the system of FIG. 2 to measure the amount of helium gas that may be contained in a sampled mixture of gases;

FIG. 5 is a diagrammatic representation of the voltage, with respect to time, produced by the comparator of FIG. 3; and FIG. 6 is a flow chart illustrating an alternate method of system operation.

DETAILED DESCRIPTION OF THE INVENTION

Illustrated in FIG. 1, and designated with the reference numeral 10, is a helium detector constructed in accordance with the teachings set forth herein. The helium detector 10 is a packaged unit measuring approximately 7"×9"×4" and weighing about five pounds. As shown, the helium detector 10 includes a housing 2, containing the component parts of the system. The top surface 4 carries the system's control panel, including a display 5 and control switches/buttons 6 for initiating measurements, or self-test operation. Attached to ends of the housing 2 is a shoulder strap 7 that facilitates carrying the system. A length of tubing 8 connects the component's interior of the housing 2 to a nozzle 9.

FIG. 2 illustrates in block diagram form the components of the helium detector 10. As shown, the helium detector 10 includes a first two-way valve V1, a second two-way valve V2, interconnected by a pump P and a sample loop 12. The valve V1 has two mutually exclusive inlets 14 and 16, and an outlet port 20 that is connected to the pump P. The inlet 14 is adapted to connect to the tubing 8 (FIG. 1) to receive the gas mixture sample to be investigated for helium content; the inlet 16 is adapted to receive air during an operational cycle that purges the system of the prior sample. The output of the pump P connects to an inlet 22 of the two-way valve V2 via the sample loop 12, which is a length of polyethylene tubing cut to a quantity sufficient to store the desired gas sample.

The valve V2 functions to selectively communicate the sample loop 12 to an inlet 28 of a column separator 30 via an outlet port 24, or to an exhaust port 26. An outlet 32 of the column separator 30 connects to a detector chamber 36 via a conduit 38. Effluent from the column separator 30 passes through the detector chamber 36 to an exhaust outlet 40 of the detector chamber.

Coupled to the detector chamber 36 is a detection circuit 42 that produces a SENSE signal on signal lines 44. The SENSE signal is a voltage that is indicative of the instantaneous thermal conductivity of the effluent passing through the detector chamber 36. Signal lines 44 couple the SENSE signal to a digital-to-analog (D/A) converter 48 which periodically samples the SENSE signal, producing a digital word for each sample taken. The digitized samples are conducted from the D/A 48 to a microprocessor 50 via an eight-bit data bus 52.

The microprocessor 50 (manufactured by Intel Corporation of Sunnyvale, Calif., and sold under the part number 8748) functions to process the received data words in a manner that will be described in greater detail below, ultimately producing information that is displayed to a user by the display 5.

The operational functions of microprocessor 50 also include control of the sample procedure—which is discussed below—through operation of the valves V1 and V2 and the pump P via an input/output (I/O) expander 60 (also manufactured by Intel Corporation and sold under the part number 8243). The I/O expander 60 is, in essence, a number of addressable output latches and input buffers, together with multiplexing and control circuitry, that function to form an extension of the I/O ports of the microprocessor 50. Binary data is coupled to the I/O expander 60 via data lines 62, held, and in turn coupled by control lines 64, 66 and 68 to appropriate driver circuitry (not shown) that control operation of the valves V1 and V2 as well as the pump P. Thus, depending upon the binary state placed on the control lines 64–68, the valve V1 will select either input line 14 or input line 16 to communication to the output line 20 of valve V1; the pump P will be placed in a pumping or non-pumping inoperative state; and the valve V2 will operate to select one of the output ports 24 or 26 (but not both) for communication with the input port 22.

The detector chamber 36 and detection circuit 42 are illustrated in greater detail in FIG. 3. As shown, the detector chamber 36 includes a pair of cavities 70 and 72, each having ports 74 and 76 formed to communicate the exterior of the detector chamber 36 thereto. The port 74 of the cavity 72 is adapted to connect to the conduit 38 (FIG. 2) to receive the effluent from column separator 30. The port 76 connects to the exhaust line 40. The ports 74 and 76 of the cavity 70 are left open to the atmosphere.

Situated in the cavities 70 and 72 are sensors 80 and 82, respectively, each formed from a thin (approximately 1 mil in diameter) platinum wire coated with alumina, and preferably matched to have substantially similar temperature characteristics. The sensors 80, 82 are connected to form a part of a bridge circuit that includes resistors R1, R2 and potentiometer R3, found in the detection circuit 42. The bridge circuit, so formed, is connected by input resistors R4 and R5 to a comparator circuit comprising differential amplifiers 84 and 86. Feedback resistances R6 and R7 set the gain of the amplifiers 84 and 86, while potentiometer R7 functions to balance the gain of the two amplifiers. The outputs of the amplifiers 84 and 86, which produce the SENSE signal, connect to the signal lines 44 that conduct the SENSE signal to the D/A 48 (FIG. 2).

As indicated above, the invention of FIGS. 1–3 finds particular applicability as a detector of helium tracer gas used to locate leaks in underground telephone cables. Leak location, using a helium gas tracer, generally proceeds as follows: A section of cable suspected of containing the leak is charged with a helium tracer gas. The ground surface route that generally overlies the suspect (buried) cable is followed, boring holes approximately every eight feet, each hole measuring about six inches in depth and two inches in diameter. A probe is inserted in the hole and the air mixture therein sampled. Using this technique it will be hoped that at least one of the holes will be found to contain a larger concentration of helium tracer gas than the other holes, indicating its close proximity to the leak from which the tracer is escaping. A hole will have a certain amount of helium because the helium will permeate somewhat through the sheath and up to the ground's surface, but more so at the leak.

The present invention fits neatly into this leak location procedure. Thus, the terminus of the probe 9 (FIG. 1) is provided for insertion into the bored holes to conduct a predetermined portion of the gas mixture found in the hole to the helium detection unit 10 to determine its helium content. The helium detector 10 performs a three-part sample/measurement/purge cycle to determine a helium content operation. This operation is illustrated in FIG. 4. A measurement cycle is initiated by activation of a control 6, generating a START signal that is applied to the microprocessor 50 and causing the microprocessor 50 to issue signals via the I/O expander 60 to begin operation of the pump P (FIG. 4—step 90). At the same time, the valves V1 and V2 are operated to place the valve V1 in a position that communicates the inlet 14 to the outlet 20, closing inlet 16. Similarly, and at the same time, valve V2 is in a position that communicates the inlet 22 to the exhaust 26. With the terminus of the probe 9 inserted in a hole (not shown), operation of the pump P will draw a sample of the gas mixture in the hole into the inlet 14, through valve V1 to pump P, into sample loop 12, and ultimately to the exhaust 26 of valve V2. The microprocessor 50 will continue this state of operation for a time (step 92) sufficient to ensure that the sample loop 12 contains a sample of the gaseous mixture taken from the bored hole—typically about 30 seconds. Microprocessor 50 will then issue command signals on the data lines 62 to the I/O expander 60, causing the valve V1 to switch its operating state, communicating inlet 16 to the outlet 20. At the same time, the state of valve V2 is also switched so that the input 22 is communicated to the output 24. The pump P continues to pump, and the sampled air mixture is moved from the sample loop 12 to and through the column separator 30 (step 94).

In the preferred embodiment of the invention, the column separator 30 has a packing that is specific to the gas anticipated, i.e., helium. The packing, which is approximately 90% activated carbon and 10% silica gel, functions to separate and order the component gases that make up the sampled gas mixture to produce an effluent containing component gases in separated fashion—with the helium component, if any, located in the initial portions of the effluent. Thus, the effluent that exits the column separator 30 at the output 32 will have the component gases of the sampled gas mixture relatively located in generally an ordered, sequential manner. The helium tracer gas, due to its small molecular size and weight, will precede the other component gases of the sampled air mixture to the detector chamber 36.

It should be noted that although the ordering algorithm used here is based on size ("macro-ordering") other algorithms are possible. For example, ordering of the component gases of the sampled gas mixture could be based upon oxidation-reduction capabilities, charge characteristics, and the like, depending upon the component gas being searched for. To use a different ordering algorithm one may need only change the packing of the column separation 30.

The effluent, comprising the separated component gases of the sampled gas mixture, is conducted by the conduit 38 to and through the cavity 72 (FIG. 3) of the detector chamber 36, and out the exhaust line 40. As illustrated in FIG. 3, a voltage V is applied to the bridge circuit containing the sensors 80 and 82, causing the aluminum windings that form the sensors to reach a temperature of approximately 200° C. The coating of alumina tends to concentrate this temperature toward the center of the windings. As the effluent from the column separator 30 passes through the cavity 72, the initial portion of that effluent, in which any helium tracer gas component of the air mixture sample will be located, will cool the sensor 82 by an amount that depends upon the thermal conductivity of the effluent. This causes a change in resistance of the sensor 82, relative to that of sensor 80, and an imbalance in the bridge circuit containing the sensors 80 and 82. The imbalance so produced is a measure of the thermal conductivity of the effluent, and will be directly related to the quantity of helium tracer gas in the effluent. The imbalance is amplified by the amplifiers 84 and 86, forming the SENSE signal that is communicated to the D/A 48 by signal lines 44.

The SENSE signal is converted to a digital representation thereof by the D/A 48, and monitored by the microprocessor 50. This monitoring process, in essence, examines the rate of change of the SENSE signal during that period of time that the effluent from the column separator 30 is expected to contain the helium tracer gas, i.e., the initial portion (FIG. 4—step 96). A predetermined time ($t_\phi$) after step 94 is initiated the microprocessor 50 samples the SENSE signal, obtaining and temporarily storing a baseline value of $S_\phi$ (step 97). At the same time the microprocessor 50 begins an integration process (step 98) that integrates the SENSE signal with respect to time. The integration process continues until the rate of change of the SENSE signal, which is continuously monitored during the integration process, drops to approximately zero or integration has been performed for a predetermined time ($t_2$), whichever occurs first (step 100), at which time the integration process terminates. If the integration terminated normally (i.e., when the rate of change of the thermal conductivity of the effluent dropped to zero), the resultant measure obtained by the integration process will be a relatively good indication of the quantity of the helium tracer gas component of the sampled gas mixture. When the conditions of step 100 are met, i.e., the rate of change drops to zero or the integration process times out, the operation then proceeds to the purge portion of the cycle (steps 102, 104).

Before continuing, the integration aspect of the measurement procedure bears further examination. Referring to FIG. 5 there is illustrated a curve 110 that generally represents the SENSE signal, i.e., the measured thermal conductivity of the first portion of the effluent passing through the cavity 72 of detector chamber 36 relative to the atmosphere in cavity 70, with that first portion containing a helium tracer component. The curve 90 is a plot of the SENSE signal (S) with respect to time (t).

At the completion of the time period indicated in FIG. 5 as $t_0$, the microprocessor commences the integration process of the SENSE signal, continuing to monitor the rate of change ds/dt (steps 98 and 100, FIG.

4). At point 114 the rate of change becomes zero, indicating the peak of the curve 110, at which time the integration process stops. The result obtained is a measurement, indicated by the cross-hatched portion of the curve 110, that is indicative of the quantity of helium tracer gas component in the sampled air mixture. This measure is adjusted (i.e., multiplied by 2 and scaled) to form a representation that is transferred to the display 54 where it is latched and displayed to a user.

The measurement cycle of FIG. 4 is completed by a purge of the system. Thus, at the step 102, the valves V1 and V2 and pump P remain in a state that continues to draw air from the atmosphere and through the column separator 30 to clear it of any extraneous helium for the next measurement cycle. At predetermined intervals the SENSE signal is sampled, and compared to the baseline amount ($S_\phi$) obtained in step 97. If the present sample is within a certain range (L) of the baseline amount, the purge cycle is complete; if not, step 102 continues.

FIG. 6 illustrates an alternative sequence of the steps that can be taken in accordance with the present invention. The steps of FIG. 6 labeled 90, 92, 94, 102 and 104 are identical to those of FIG. 4. However, the steps 96, 97, 98 and 100 of FIG. 4 are replaced with steps 96A, 98A and 100A in FIG. 6. The alternate method proceeds, up to step 94, as explained above with reference to FIG. 4, and, although not shown in FIG. 6, the baseline amount ($S_0$) is obtained. At step 96A, the rate of change of the SENSE signal commences to be monitored. When that rate of change exceeds a predetermined amount (K), the integration process is initiated (step 98A). Integration of the SENSE signal proceeds until the rate of change of the SENSE signal is approximately zero (step 100A), at which time the purge cycle is entered at step 102. If the rate of change of the SENSE signal never exceeds K, the integration steps 98A, 100A are never entered, and system operation proceeds directly from 96A to step 102. Steps 102 and 104 are the same as those described with respect to FIG. 4.

In summary, there has been disclosed a method and apparatus for detecting a helium tracer gas that is simple and quick to use, inexpensive to manufacture, and adapted for field use. While a full and complete disclosure of the preferred and alternate embodiments of the invention are set forth, various modifications, alternate constructions and equivalents may be employed without departing from the true spirit and scope of the invention. For example, it will be evident to those skilled in this art that the configuration of the column separator 30 can be tailored to locating and measuring gases other than helium. One reconfiguration would be to use "polar packing" to effect gas separation by relative surface charge on the molecules that make up the component gases contained in a mixture, retarding certain gases relative to others so that the searched for gas will appear preferably first in time in the effluent. Separation can also position the searched for gas further down the line in the effluent and changes in the rate of change of a monitored physical property used to count when that portion of the effluent containing the searched for gas is encountered. This technique, however, requires the presence in the effluent of the component gases that precede the searched for gas by the ordering established by the column separator 30. For this reason it is preferred that the ordering performed by the column separator place the searched for gas at the initial portion of the effluent.

Therefore, this disclosure and illustrations should not be construed as limiting the scope of the invention, which is defined by the appended claims.

Set forth below in Table I is a source code listing of the microprocessor program that causes the system to operate in the manner above-described with reference to FIG. 4.

TABLE I

```
MCS48 EDITOR/ASSEMBLER REV II - APPLE VERSION
SOURCE : HELVER3

NO.  ADD.  CODE         INSTRUCTION 1    0000                ;HELIUM VER 3.1
2    0000                ;DATE 5-13-85
3    0000                ;VARIABLE PURGE
4    0000                ;ADDING FLOW DIAGNOSTICS
5    0000                ;BLANK ZERO AT HIGH SCALE
6    0000                ;EXPAND AUTO ZEROING
7    0000                ;24,25,26,27 : DISPLAY MEMORY
8    0000                ;32,33 : ANALOG DATA
9    0000                ;39    : ZERO DATA
10   0000                ;40    : PORT2 DATA
11   0000                ;35,36 : BASE DATA
12   0000                ;FLAG 0 - 1 :HIGH SCALE
13   0000                     ORG #0         ;RESET
14   0000  15               DIS I
15   0001  35               DIS TCNTI
16   0002                ;PORT 1: AUTO ZERO - PRESET VALUE 80H
17   0002                ;PORT 4: LEDS - 0= SAMPLE - 1=PURGE - 2= READ
18   0002                ;PORT 5: DISPLAY = 0= CLOCK - 1=DATA - 2= GAIN ( 0=1% SCALE)
19   0002                ;PORT 6: CONTROL = 0=POWER* - 1=VALVE1* - 2=VALVE2* - 3=HOLD (
20   0002                ;PORT 7: INPUT ERROR BIT 0 (RESERVED)
21   0002                ;------------------------------------------
22   0002  BA24             MOV R2,#36     ;36 CLOCKS
23   0004  85               CLR F0
24   0005  95               CPL F0
```

```
25  0006 27      CLK36: CLR A            ;CLEAR DISPLAY
26  0007 3D             MOVD P5,A
27  0008 4301           ORL A,#1
28  000A 3D             MOVD P5,A
29  000B EA06           DJNZ R2,CLK36
30  000D B818           MOV R0,#24       ;CLEAR BUFFER
31  000F 27             CLR A
32  0010 BA14           MOV R2,#20
33  0012 A0      CLEAR: MOV @R0,A
34  0013 18             INC R0
35  0014 EA12           DJNZ R2,CLEAR
36  0016 B827           MOV R0,#39
37  0018 2380           MOV A,#80H       ;ZERO PRESET VALUE
38  001A A0             MOV @R0,A
39  001B 39             OUTL P1,A
40  001C 2302   STEST:  MOV A,VALV2      ;POWER AND VALUE 2
41  001E 3E             MOVD P6,A
42  001F 2307           MOV A,#7
43  0021 3C             MOVD P4,A        ;ALL LEDS ON
44  0022 BD64           MOV R5,#100      ;COUNT FROM 100
45  0024 FD             MOV A,R5
46  0025 3497           CALL HXCONV
47  0027 5400           CALL DXFER
?
48  0029 CD             DEC R5
49  002A 341B           CALL SEC30
50  002C BE14           MOV R6,#20       ;CAL. COUNTER
51  002E 230A           MOV A,VHLT2      ;HOLD #2
52  0030 3E             MOVD P6,A
53  0031 563D   ST2:    JT1 ST1          ;SWITCH PRESS ?
54  0033 EE3D           DJNZ R6,ST1
55  0035 BB4B           MOV R3,#75
56  0037 744D           CALL BCOMP       ;COMPARE R5&S5
57  0039 763D           JF1 ST1          ;IGNORED IF R5<S5
58  003B 443F           JMP TEST         ;ENTER CAL MODE
59  003D FD      ST1:   MOV A,R5
60  003E 3497           CALL HXCONV
61  0040 5400           CALL DXFER
62  0042 BF1E           MOV R7,#30
63  0044 341D           CALL TIMER
64  0046 2329           MOV A,#41        ;SENSOR TEST
65  0048 DD             XRL A,R5
66  0049 C659           JZ ST3
67  004B 2328           MOV A,#40
68  004D DD             XRL A,R5
69  004E C65D           JZ ST4
70  0050 2314           MOV A,#20
71  0052 DD             XRL A,R5         ;VALUE 2
72  0053 C66E           JZ ST5
73  0055 ED31   SCOUNT: DJNZ R5 ST2
74  0057 0489           JMP WAIT
75  0059 14C6   ST3:    CALL AUTO0       ;REZERO AFFECTED
76  005B 0455           JMP SCOUNT
77  005D 14DB   ST4:    CALL INCRE
78  005F 740A           CALL ADC
79  0061 AA             MOV R2,A         ;TEST VALUE 1
80  0062 27             CLR A
81  0063 3E             MOVD P6,A        ;VALUE 1
82  0064 740A           CALL ADC
83  0066 DA             XRL A,R2
84  0067 C67D           JZ ST4ERR
85  0069 230A           MOV A,VHLT2
86  006B 3E             MOVD P6,A
87  006C 0455           JMP SCOUNT
88  006E 14C6   ST5:    CALL AUTO0
89  0070 740A           CALL ADC         ;TEST VALUE 2
90  0072 AA             MOV R2,A
91  0073 230E           MOV A,#EH        ;VALUE 2
92  0075 3E             MOVD P6,A
93  0076 740A           CALL ADC
94  0078 DA             XRL A,R2
?
```

```
95  0079 C683            JZ STSERR
96  007B 0455            JMP SCOUNT
97  007D BD28   ST4ERR:  MOV R5,#40
98  007F 2304            MOV A,#4
99  0081 6423            JMP STERR
100 0083 BD14   STSERR:  MOV R5,#20
101 0085 2302            MOV A,#2
102 0087 6423            JMP STERR
103 0089 27     WAIT:    CLR A
104 008A B828            MOV R0,#40
105 008C A0              MOV @R0,A          ;LOW SCALE
106 008D 3D              MOVD P5,A
107 008E 3C              MOVD P4,A          ;ALL LED OFF
108 008F 230F            MOV A,#0FH
109 0091 3E              MOVD P6,A          ;POWER OFF
110 0092 FD              MOV A,R5
111 0093 3497            CALL HXCONV
112 0095 5400            CALL DXFER
113 0097 5689            JT1 WAIT
114 0099 85              CLR F0
115 009A          ;START SAMPLING CYCLE
116 009A 04     VALV1:   EQU #04
117 009A 0C     VHLT1:   EQU #CH
118 009A 02     VALV2:   EQU #2
119 009A 0A     VHLT2:   EQU #AH
120 009A 2304            MOV A,VALV1
121 009C 3E              MOVD P6,A
122 009D 2301            MOV A,#1
123 009F 3C              MOVD P4,A          ;SAMPLE LED
124 00A0 341B            CALL SEC30         ;DELAY 1S
125 00A2 230C            MOV A,VHLT1        ;SEND HOLD
126 00A4 3E              MOVD P6,A
127 00A5 27              CLR A
128 00A6 3497            CALL HXCONV
129 00A8 5400            CALL DXFER
130 00AA BE1E            MOV R6,#30         ;SAMPLING TIME
131 00AC 27     DLY28:   CLR A
132 00AD 3497            CALL HXCONV
133 00AF 5400            CALL DXFER
134 00B1 341B            CALL SEC30
135 00B3 EEAC            DJNZ R6,DLY28
136 00B5 2302            MOV A,VALV2
137 00B7 3E              MOVD P6,A          ;TURN VALVE 2
138 00B8 2304            MOV A,#4           ;READ LED
139 00BA 3C              MOVD P4,A
140 00BB 341B            CALL SEC30
141 00BD 230A            MOV A,VHLT2
142 00BF 3E              MOVD P6,A
143 00C0 341B            CALL SEC30
144 00C2 14C6            CALL AUTOO
145 00C4 2428            JMP DETEK
146 00C6 740A   AUTOO:   CALL ADC
147 00C8 AA              MOV R2,A
148 00C9 03F6            ADD A,#F6H         ;COMPARE 10
149 00CB C6D6            JZ ZEROK
150 00CD E6D7            JNC LES10
151 00CF FA              MOV A,R2
152 00D0 03EC            ADD A,#ECH         ;COMPARE 20
153 00D2 C6D6            JZ ZEROK
154 00D4 F6EB            JC BIG20
155 00D6 83     ZEROK:   RET
156 00D7 14EC   LES10:   CALL DECRE
157 00D9 04C6            JMP AUTOO
158 00DB B827   INCRE:   MOV R0,#39
159 00DD F0              MOV A,@R0
160 00DE 53FF            ANL A,#FFH
161 00E0 96E4            JNZ INCOK
162 00E2 04F8            JMP ERROR
163 00E4 10     INCOK:   INC @R0
164 00E5 F0              MOV A,@R0
165 00E6 39              OUTL P1,A          ;ZERO IT
```

```
166  00E7 83            RET
167  00E8 14DB  BIG20:  CALL INCRE
168  00EA 04C6          JMP AUTOO
169  00EC B827  DECRE:  MOV R0,#39
170  00EE F0            MOV A,@R0      ;GET DATA
171  00EF 53FF          ANL A,#FFH
172  00F1 C6F8          JZ ERROR
173  00F3 F0            MOV A,@R0
174  00F4 07            DEC A
175  00F5 A0            MOV @R0,A
176  00F6 39            OUTL P1,A      ;SEND IT OUT
177  00F7 83            RET
178  00F8              ;ERROR CONDITION : CANNOT ZERO
179  00F8              ;SHUT POWER OFF - SEND MESSAGE "ERR." (FLASHING)
180  00F8 B818  ERROR:  MOV R0,#24
181  00FA B050          MOV @R0,#50H   ;CHAR "R"
182  00FC 18            INC R0
183  00FD B050          MOV @R0,#50H   ;CHAR "R"
184  00FF 18            INC R0
185  0100 B079          MOV @R0,#79H   ;CHAR "E"
186  0102 18            INC R0
187  0103 B000          MOV @R0,#0     ;BLANK
188  0105 5400          CALL DXFER     ;DISPLAY IT
189  0107 341B          CALL SEC30
190  0109 B818          MOV R0,#24     ;BLANK DISPLAY
191  010B 230F          MOV A,#0FH     ;POWER OFF
192  010D 3E            MOVD P6,A
193  010E 27            CLR A
194  010F BA04          MOV R2,#4
195  0111 A0    BLANK:  MOV @R0,A
196  0112 18            INC R0
197  0113 EA11          DJNZ R2,BLANK
198  0115 5400          CALL DXFER
199  0117 341B          CALL SEC30
200  0119 04F8          JMP ERROR      ;REPEAT UNTIL OFF
201  011B              ;--------------------------------
202  011B BF31  SEC30:  MOV R7,#49     ;1 SEC
203  011D 27    TIMER:  CLR A
204  011E 62            MOV T,A
205  011F 55            STRT T         ;START TIMER
206  0120 1624  TWAIT:  JTF TIRET
207  0122 2420          JMP TWAIT
208  0124 65    TIRET:  STOP TCNT
209  0125 EF1D          DJNZ R7,TIMER
210  0127 83            RET
211  0128             ;READING ANALOG DATA - LATCH OUT PEEK
212  0128 BF0E  DETEK:  MOV R7,#14
213  012A 27            CLR A
214  012B AE            MOV R6,A
215  012C 62            MOV T,A
216  012D 55            STRT T
217  012E 740A  BEGIN:  CALL ADC
218  0130 B924          MOV R1,#36
219  0132 A1            MOV @R1,A      ;BASE DATA
220  0133 AB            MOV R3,A
221  0134 740A  PEAK:   CALL ADC       ;2ND DATA IN R4R5
222  0136 AD            MOV R5,A
223  0137 744D          CALL BCOMP
224  0139 765A          JF1 PTIME      ;IGNORED IF R3>R5
225  013B B824          MOV R0,#36     ;BASE
226  013D B64A          JF0 GSET       ;GAIN SET
227  013F F0            MOV A,@R0
228  0140 17            INC A
229  0141 A9            MOV R1,A       ;TEMP SAVE
230  0142 DD            XRL A,R5       ;IGNORED IF 1 DIFFER
231  0143 C65A          JZ PTIME
232  0145 F9            MOV A,R1       ;IGNORED IF 2 DIFF
233  0146 17            INC A
234  0147 DD            XRL A,R5
235  0148 C65A          JZ PTIME
```

```
236 014A F0        GSET:   MOV A,@R0
237 014B 37                CPL A              ;PERFORM R5-#36
238 014C 17                INC A
239 014D 6D                ADD A,R5
240 014E AA                MOV R2,A           ;RESULT IN R2
241 014F 039B              ADD A,#155         ;RANGE FROM 0 TO 100
242 0151 F686              JC GAIN
243 0153 FA                MOV A,R2
244 0154 3497      DNEXT:  CALL HXCONV
245 0156 5400              CALL DXFER
246 0158 FD                MOV A,R5
247 0159 AB                MOV R3,A
248 015A EE34      PTIME:  DJNZ R6,PEAK
249 015C EF34              DJNZ R7,PEAK
250 015E 2302              MOV A,#2
251 0160 3C                MOVD P4,A          ;PURGE LED
252 0161 B928      PURGE:  MOV R1,#40
253 0163 F1                MOV A,@R1
254 0164 53FB              ANL A,#FBH
255 0166 A1                MOV @R1,A
256 0167 3D                MOVD P5,A
257 0168 740A              CALL ADC
258 016A B677              JF0 RWAIT          ;GAS STILL EXISTED
259 016C AD                MOV R5,A           ;TEMP. SAVE
260 016D B924              MOV R1,#36         ;BASE DATA
261 016F F1                MOV A,@R1
262 0170 030A              ADD A,#10          ;ADJUST VALUE
263 0172 AB                MOV R3,A
264 0173 744D              CALL BCOMP
265 0175 7680              JF1 PEND           ;PURGE ENDED
266 0177 B825     RWAIT:   MOV R0,#37         ;LAST DATA
267 0179 F0                MOV A,@R0
268 017A 3497              CALL HXCONV
269 017C 5400              CALL DXFER
270 017E 2461              JMP PURGE
271 0180 B825     PEND:    MOV R0,#37
272 0182 F0                MOV A,@R0
273 0183 AD                MOV R5,A
274 0184 0489              JMP WAIT
275 0186 B828     GAIN:    MOV R0,#40         ;SET SCALE
276 0188 F0                MOV A,@R0
277 0189 4304              ORL A,#4
278 018B A0                MOV @R0,A
279 018C 3D                MOVD P5,A
280 018D 85                CLR F0             ;SET FLAG
281 018E 95                CPL F0
282 018F 740A              CALL ADC
283 0191 B824              MOV R0,#36
284 0193 A0                MOV @R0,A
285 0194 AD                MOV R5,A
286 0195 2454              JMP DNEXT
287 0197             ;----------------------------------
288 0197             ;CONVERT (A) TO DECIMAL
289 0197             ;R4 :100', R3: 10', R2-1'S
290 0197 AA        HXCONV: MOV R2,A
291 0198 B825              MOV R0,#37
292 019A A0                MOV @R0,A
293 019B BB00              MOV R3,#0
294 019D BC00              MOV R4,#0
295 019F 239C     AD100:   MOV A,#9CH         ;2'S COMP OF 100
296 01A1 6A                ADD A,R2
297 01A2 E6A8              JNC AD10
298 01A4 AA                MOV R2,A           ;SAVE BACK
299 01A5 1C                INC R4
300 01A6 249F              JMP AD100
301 01A8 B6B3     AD10:    JF0 AD100C         ;JUMP UPPER SCALE
302 01AA 23F6     AD100N:  MOV A,#F6H         ;2'S COMP OF 10
303 01AC 6A                ADD A,R2
304 01AD E6BC              JNC ADUNIT
305 01AF AA                MOV R2,A
306 01B0 1B                INC R3
```

```
307 01B1 24AA            JMP  AD10ON
308 01B3 FC     AD10OC:  MOV  A,R4       ;CHECK R4
309 01B4 D300            XRL  A,#0
310 01B6 96AA            JNZ  AD10ON
311 01B8 BC80            MOV  R4,#80H    ;SET BIT 7
312 01BA 24AA            JMP  AD10ON
313 01BC B6E1   ADUNIT:  JF0  AD1OCK
314 01BE B818   ADUON:   MOV  R0,#24     ;R0-POINTER
315 01C0 FA              MOV  A,R2       ;GET CONVERT DATA
316 01C1 E3              MOVP3 A,@A
317 01C2 A0              MOV  @R0,A
318 01C3 18              INC  R0
319 01C4 FB              MOV  A,R3
320 01C5 F2DB            JB7  NOT10
321 01C7 E3              MOVP3 A,@A      ;GET 2ND DATA
322 01C8 A0     D10:     MOV  @R0,A      ;SAVE IT
323 01C9 18              INC  R0
324 01CA FC              MOV  A,R4
325 01CB F2DE            JB7  NOT100
326 01CD E3              MOVP3 A,@A      ;3RD DATA
327 01CE A0     D100:    MOV  @R0,A
328 01CF 18              INC  R0
329 01D0 B000            MOV  @R0,#0
?
330 01D2 B6DA            JF0  DSET
331 01D4 B819            MOV  R0,#25     ;DEC. POINT
332 01D6 F0              MOV  A,@R0
333 01D7 4380            ORL  A,#80H
334 01D9 A0              MOV  @R0,A
335 01DA 83     DSET:    RET
336 01DB 27     NOT10:   CLR  A
337 01DC 24C8            JMP  D10
338 01DE 27     NOT100:  CLR  A
339 01DF 24CE            JMP  D100
340 01E1 FB     AD1OCK:  MOV  A,R3       ;CHECK IF R3=0
341 01E2 D300            XRL  A,#0
342 01E4 96BE            JNZ  ADUON      ;RETURN IF R3#0
343 01E6 FC              MOV  A,R4
344 01E7 D380            XRL  A,#80H
345 01E9 96BE            JNZ  ADUON
346 01EB BB80            MOV  R3,#80H    ;SET BIT 7
347 01ED 24BE            JMP  ADUON
348 01EF          ;TRANSFER DATA IN #24,25,26,27 TO DISPLAY
349 0200                 ORG  #200H
350 0200 B928   DXFER:   MOV  R1,#40
351 0202 F1              MOV  A,@R1
352 0203 53FE            ANL  A,#FEH     ;CLK=0
353 0205 4302            ORL  A,#2       ;DATA=1
354 0207 3D              MOVD P5,A
355 0208 4301            ORL  A,#1       ;CLK=1
356 020A 3D              MOVD P5,A
357 020B 8611            JNI  DOK
358 020D B81B            MOV  R0,#27     ;LOW BATT
359 020F B002            MOV  @R0,#2
360 0211 B818   DOK:     MOV  R0,#24
361 0213 BA04            MOV  R2,#4
362 0215 BB08   DISPL:   MOV  R3,#8      ;8 CLKS
363 0217 F1     DLOOP:   MOV  A,@R1
364 0218 53FE            ANL  A,#FEH     ;CLK=0
365 021A 3D              MOVD P5,A
366 021B F0              MOV  A,@R0      ;GET DATA
367 021C 67              RRC             ;SHIFT RIGHT
368 021D A0              MOV  @R0,A      ;SAVE BACK
369 021E F625            JC   DHI
370 0220 F1              MOV  A,@R1
371 0221 53FC            ANL  A,#FCH     ;DATA=0
372 0223 442A            JMP  NDATA
373 0225 F1     DHI:     MOV  A,@R1
374 0226 53FC            ANL  A,#FCH
375 0228 4302            ORL  A,#2       ;DATA=1
376 022A 3D     NDATA:   MOVD P5,A
?
```

```
377 022B 4301           ORL  A,#1        ;CLK=1
378 022D 3D             MOVD P5,A
379 022E EB17           DJNZ R3,DLOOP
380 0230 18             INC  R0
381 0231 EA15           DJNZ R2,DISPL
382 0233 BA03           MOV  R2,#3       ;LAST 3 CLK
383 0235 F1     CLOCK:  MOV  A,@R1
384 0236 53FC           ANL  A,#FCH
385 0238 3D             MOVD P5,A
386 0239 4301           ORL  A,#1
387 023B 3D             MOVD P5,A
388 023C EA35           DJNZ R2,CLOCK
389 023E 83             RET
390 023F          ;------------------------------
391 023F B818   TEST:   MOV  R0,#24
392 0241 B038           MOV  @R0,#38H    ;"L"
393 0243 18             INC  R0
394 0244 B077           MOV  @R0,#77H    ;"A"
395 0246 18             INC  R0
396 0247 B039           MOV  @R0,#39H    ;"C"
397 0249 5400           CALL DXFER
398 024B 341B           CALL SEC30
399 024D 341B           CALL SEC30
400 024F B827           MOV  R0,#39
401 0251 2380           MOV  A,#80H      ;ZERO
402 0253 A0             MOV  @R0,A
403 0254 39             OUTL P1,A
404 0255 3C             MOVD P4,A        ;LED OFF
405 0256 2301           MOV  A,#1
406 0258 3497           CALL HXCONV
407 025A 5400           CALL DXFER
408 025C 2304           MOV  A,VALV1     ;VALUE 1
409 025E 3E             MOVD P6,A
410 025F 565F   WT1:    JT1  WT1
411 0261 4661   WNT1:   JNT1 WNT1
412 0263 230C           MOV  A,VHLT1
413 0265 3E             MOVD P6,A
414 0266 2302           MOV  A,#2
415 0268 3497           CALL HXCONV
416 026A 5400           CALL DXFER
417 026C 566C   WT2:    JT1  WT2
418 026E 466E   WNT2:   JNT1 WNT2
419 0270 2303           MOV  A,#3
420 0272 3497           CALL HXCONV
421 0274 5400           CALL DXFER
422 0276 2302           MOV  A,VALV2
423 0278 3E             MOVD P6,A
424 0279 5679   WT3:    JT1  WT3
425 027B 467B   WNT3:   JNT1 WNT3
426 027D 230A           MOV  A,VHLT2
427 027F 3E             MOVD P6,A
428 0280 2304           MOV  A,#4
429 0282 3497           CALL HXCONV
430 0284 5400           CALL DXFER
431 0286 5686   WT4:    JT1  WT4         ;COMPLETED #4
432 0288 4688   WNT4:   JNT1 WNT4
433 028A 85     TEST5:  CLR  F0          ;BACK TO LOW SCALE
434 028B 7442           CALL TEST4
435 028D 568A           JT1  TEST5
436 028F 468F   WNT5:   JNT1 WNT5
437 0291 54B8   TEST6:  CALL RAMP
438 0293 5691           JT1  TEST6
439 0295 4695   WNT6:   JNT1 WNT6
440 0297 B828   TEST7:  MOV  R0,#40
441 0299 2304           MOV  A,#4        ;GAIN SET
442 029B A0             MOV  @R0,A
443 029C 3D             MOVD P5,A
444 029D 85             CLR  F0
445 029E 95             CPL  F0
446 029F 54B8           CALL RAMP
447 02A1 5697           JT1  TEST7
```

```
448 02A3 2307    TEST8:   MOV  A,#7
449 02A5 3C               MOVD P4,A       ;LEDS ON
450 02A6 341B             CALL SEC30
451 02A8 56A3             JT1  TEST8
452 02AA 27               CLR  A
453 02AB 3C               MOVD P4,A
454 02AC B827             MOV  R0,#39
455 02AE B080             MOV  @R0,#80H
456 02B0 18               INC  R0
457 02B1 A0               MOV  @R0,A
458 02B2 3497             CALL HXCONV
459 02B4 5400             CALL DXFER
460 02B6 0489             JMP  WAIT
461 02B8 14DB    RAMP:    CALL INCRE
462 02BA 7442             CALL TEST4
463 02BC B827             MOV  R0,#39
464 02BE F0               MOV  A,@R0
465 02BF D3FF             XRL  A,#FFH
466 02C1 96B8             JNZ  RAMP
467 02C3 14EC    RAMPDN:  CALL DECRE
468 02C5 7442             CALL TEST4
469 02C7 B827             MOV  R0,#39
470 02C9 F0               MOV  A,@R0
471 02CA D301             XRL  A,#1
472 02CC 96C3             JNZ  RAMPDN
473 02CE 83               RET
474 0300             ORG #300H
475 0300             ;THIS IS PAGE 3, RESERVED FOR DATA MEMORY
476 0300 3F               DB   #3FH      ;0
477 0301 06               DB   #6H       ;1
478 0302 5B               DB   #5BH      ;2
479 0303 4F               DB   #4FH      ;3
480 0304 66               DB   #66H      ;4
481 0305 6D               DB   #6DH      ;5
482 0306 7D               DB   #7DH      ;6
483 0307 07               DB   #07H      ;7
484 0308 7F               DB   #7FH      ;8
485 0309 67               DB   #67H      ;9
486 030A           ;-------------------------
487 030A           ;ADC ROUTINE
488 030A D5      ADC:     SEL  RB1
489 030B BE0F             MOV  R6,#15
490 030D 741E             CALL AREAD     ;READ ANALOG
491 030F AB               MOV  R3,A      ;SAVE IT
492 0310 741E    ACONT:   CALL AREAD     ;SECOND READ
493 0312 AD               MOV  R5,A
494 0313 744D    ACON2:   CALL BCOMP     ;COMP R2R3-R4R5
495 0315 7619             JF1  ANEXT
496 0317 FD               MOV  A,R5
497 0318 AB               MOV  R3,A
498 0319 EE10    ANEXT:   DJNZ R6,ACONT
499 031B FB               MOV  A,R3
500 031C C5               SEL  RB0
501 031D 83               RET
502 031E 91      AREAD:   MOVX @R1,A     ;SEND CONVERT
503 031F 361F    ALOOP:   JT0  ALOOP     ;WAIT
504 0321 81               MOVX A,@R1
505 0322 83               RET
506 0323           ;-----------------
507 0323 AE      STERR:   MOV  R6,A
508 0324 85               CLR  F0
509 0325 95               CPL  F0
510 0326 230F             MOV  A,#FH     ;POWER OFF
511 0328 3E               MOVD P6,A
512 0329 FD      FLASH:   MOV  A,R5
513 032A 3497             CALL HXCONV
514 032C 5400             CALL DXFER
515 032E FE               MOV  A,R6
516 032F 3C               MOVD P4,A
517 0330 341B             CALL SEC30
```

```
518 0332 B818            MOV  R0,#24    ;BLANK
519 0334 BA04            MOV  R2,#4
520 0336 27              CLR  A
521 0337 A0       SFLASH:MOV  @R0,A
522 0338 18              INC  R0
523 0339 EA37            DJNZ R2 SFLASH
524 033B 3C              MOVD P4,A
525 033C 5400            CALL OXFER
526 033E 341B            CALL SEC30
527 0340 6429            JMP  FLASH
528 0342 740A     TEST4: CALL ADC
529 0344 3497            CALL HXCONV
530 0346 5400     DATA:  CALL OXFER
531 0348 BF05            MOV  R7,#5
532 034A 341D            CALL TIMER
533 034C 83              RET
534 034D          ;------------------------------
535 034D          ;COMPARE R3 & R5 - RETURN F1=1 IF R3>R5
536 034D A5       BCOMP: CLR  F1
537 034E FB              MOV  A,R3
538 034F 37              CPL  A
539 0350 17              INC  A
540 0351 6D              ADD  A,R5
541 0352 E555            JNC  R3>R5
542 0354 83              RET
543 0355 B5       R3>R5: CPL  F1
544 0356 83              RET
```

ERROR - 0

I claim:

1. A method for detecting a suspect component of gas in a gas mixture containing a plurality of component gases mixed with ambient atmosphere, comprising the steps of:

providing a fixed phase separator configured to produce an effluent in which the first component of gas is positionally consigned to a leading and first portion of the effluent relative to the remaining component gases of the mixture;

passing atmosphere through a fixed-phase separator;

commencing the passing of the gas mixture through said fixed-phase separator whereby an effluent in which the first component gas is positionally consigned to a predetermined portion of the effluent relative to the remaining component gases of the gas mixture;

monitoring the rate of change of the thermal conductivity of the effluent at a point after said fixed phase separator during a specific time interval from said commencing step to enable the portion of the effluent to which the first component gas is positionally consigned to pass the monitoring point within said time interval;

monitoring the rate of change of the thermal conductivity of the ambient atmosphere simultaneously with the monitoring of the rate of change of the thermal conductivity of the effluent;

comparing the rate of change of the thermal conductivity of the effluent with the rate of change of the thermal conductivity of the ambient atmosphere to obtain a thermal conductivity comparison;

measuring the thermal conductivity comparison from a time within said time interval wherein said thermal conductivity comparison exceeds a predetermined rate of charge until the rate of change of the thermal conductivity comparison becomes approximately zero; and, integrating said rate of change of said thermal conductivity comparison from said predetermined rate of change until said rate of change becomes zero to produce therefrom a measure of the quantity of the first component gas in the gas mixture.

2. Apparatus for detecting presence of a predetermined one of a plurality of component gases contained in a gas mixture including ambient atmosphere, the apparatus comprising:

sampling means for receiving and holding said gas mixture for analysis;

pump means for moving said gas sample from said sample means at a selected time interval;

separating means adapted to receive the gas mixture from said pump means for producing an effluent in which the predetermined component gas is locatable as the leading component;

thermal conductivity detector means coupled to receive the effluent to produce therefrom a signal indicative of the thermal conductivity of said leading component of gas;

said thermal conductivity detector means including a first thermal conductivity detector communicated to said effluent, a second thermal conductivity detector communicated to said ambient atmosphere, and comparison circuit means communicated to an output for outputting a thermal conductivity comparison signal between said thermal conductivity detectors;

first circuit means operatively coupled to said output of said thermal conductivity detector means for receiving said thermal conductivity comparison signal to measure a predetermined rate of change of said output during a time period corresponding to the time-locatable position of the predetermined component gas from said selected time interval;

second circuit means connected to said output of said thermal conductivity detector means to measure said rate of change of said thermal conductivity comparison signal from said predetermined rate of change until said rate of change approaches zero; integration means for integrating said rate of change between said predetermined rate of change until said rate of change approaches zero to produce therefrom a measure indicative of the quantity of the predetermined component gas in the gas mixture.

3. The apparatus of claim 2, wherein the separating means includes a fixed-phase column separator.

4. The apparatus of claim 2, wherein the fixed-phase column separator includes a packing formed from approximately 90% activated carbon and approximately 10% silica gel.

5. The apparatus of claim 2, wherein physical property is thermal conductivity.

* * * * *